United States Patent
Precopio

(10) Patent No.: US 6,793,931 B2
(45) Date of Patent: Sep. 21, 2004

(54) ECTOPARASITE ASPHYXIATOR COMPOSITIONS AND METHODS FOR THEIR APPLICATIONS

(75) Inventor: Michael J Precopio, Collegeville, PA (US)

(73) Assignee: Summers Laboratories, Inc., Collegeville, PA (US)

( * ) Notice: Subject to any disclaimer, the term of this patent is extended or adjusted under 35 U.S.C. 154(b) by 0 days.

(21) Appl. No.: 10/195,048

(22) Filed: Jul. 11, 2002

(65) Prior Publication Data

US 2004/0009203 A1 Jan. 15, 2004

(51) Int. Cl.[7] .......................... A01N 25/02; A61K 7/075
(52) U.S. Cl. .................... 424/406; 424/70.1; 424/70.31
(58) Field of Search ............................... 424/406, 70.1, 424/70.31, 405

(56) References Cited

U.S. PATENT DOCUMENTS

| | | | |
|---|---|---|---|
| 4,927,813 A | 5/1990 | Bernstein | |
| 5,211,941 A | 5/1993 | Komori et al. | |
| 5,292,504 A | * 3/1994 | Cardin et al. | 514/65 |
| 5,783,202 A | 7/1998 | Tomlinson et al. | |
| 5,858,383 A | 1/1999 | Precopio | |
| 6,139,859 A | * 10/2000 | Precopio | 424/406 |
| 6,524,604 B1 | * 2/2003 | Ozelkan et al. | 424/406 |

OTHER PUBLICATIONS

Pediatric News, Jun. 1997 "Getting Rid of the Head Lice From Hell", p. 36 (Dates).
Clear Products Information Flier, Dated Jun. 19, 1997.
Dermatology Times, May 1997, pp. 3–4.
Milks, Practical Veterinary Pharmacology Dated 1949.
Meinking, TL, Burkhart CG, Burkhart CN. Ectoparasitic Disease in Dermatology: Reassessment of Scabies and Pediculosis *Advances in Dermatology*, Chapter 3, p. 99 Mosby 1999.
Drug Store News, CP44, Aug. 30, 1999.

* cited by examiner

*Primary Examiner*—Jyothsna Venkat
(74) *Attorney, Agent, or Firm*—Henry E. Millson, Jr.

(57) ABSTRACT

Water-soluble or water-dispersible, substantially air-impermeable, pharmacologically acceptable, liquid barrier compositions for treating ectoparasite infestations on animal skin and hair, wherein the compositions contain at least one monohydric aralkyl alcohol to prevent the ectoparasites from closing their respiratory systems.

38 Claims, No Drawings

ECTOPARASITE ASPHYXIATOR COMPOSITIONS AND METHODS FOR THEIR APPLICATIONS

FIELD OF THE INVENTION

This invention relates to compositions and methods for treating ectoparasite infestations on mammalian bodies, particularly human head lice infestations.

BACKGROUND OF THE INVENTION

Current methods for the treatment of ectoparasites, e.g. lice, typically utilize insecticidal compositions which are available in both prescription and over-the-counter formulations. Such compositions generally include one or more of the active ingredients benzyl benzoate, pyrethrin, permithrin, and lindane. Dispensing formulations include lotions, creams, shampoos, cream rinses, and gels.

However, increasing numbers of ectoparasite infections, especially head lice, that are resistant to the above insecticides have been reported in the medical literature.

Alternative insecticidal treatments such as the use of malathion, ivermectin, and a combination of trimethoprirn and sulfamethazole have been tried, but usually only with mixed results.

Another approach that has been reported and which is at least partially effective is the use of a topical petrolatum-containing product, which suffocate the parasites when left on the head for a prolonged period of time. However, removal of the petrolatum from the head and hair has proven to be a difficult problem, often taking about ten days for complete removal.

Oil based occlusive treatments have been observed to significantly immobilize and coat the lice long enough for asphyxiation to occur. However, some adult lice survived even after an overnight treatment. Meinking, T L, Burkhart C G, Burkhart C N, Ectoparasitic Disease in Dermatology: Reassessment of Scabies and Pediculosis, *Advances in Dermatology,* Chapter 3, pp 99, Mosby Inc. 1999.

Head lice have been on the increase in the recent past, in large part due to the fact that they have become more tolerant or resistant to conventional treatments. For this reason children are being over-treated with pesticide-containing products as well as other unconventional treatments in an effort to control this epidemic. Many parents and health professionals have turned to unproven and generally ineffective alternative products such as mayonnaise, olive oil, etc. Unfortunately, others have turned to very dangerous alternatives such as gasoline, kerosene or traumatizing measures such as head shaving.

It was recently discovered by the present inventor that ectoparasites on animal skin can be treated successfully by a method comprising the steps of:
I) applying to the skin affected by ectoparasites a water-soluble or water-dispersible, substantially air-impermeable liquid barrier composition;
II) leaving the composition in contact with the skin until the ectoparasites have been killed by suffocation; and
III) removing the composition and the dead ectoparasites from the skin.

See U.S. Pat. Nos. 5,858,383 and 6,139,859.

SUMMARY OF THE INVENTION

Other than in the operating examples, or where otherwise indicated, all numbers expressing quantities of ingredients used herein are to be understood as modified in all instances by the term "about".

It has now been discovered that water-soluble or water-dispersible, substantially air-impermeable liquid barrier compositions that contain monohydric aralkyl alcohols effectively prevent the ectoparasites from closing their respiratory systems (breathing apparatus), called breathing spiracles in lice.

Ectoparasites such as lice, especially head lice, can normally defend against asphyxiation for prolonged periods of time, even up to 12 hours, by closing their spiracles. With the compositions of the invention asphyxiation occurs in very much shorter periods of time, e.g. in less than 45 minutes, usually between 10 and 15 minutes. This is much faster than expected since occlusion of the lice with other materials and compositions will take at least several hours to result in asphyxiation.

The invention also relates to the use of the compositions of the invention for treating ectoparasites on animal skin and hair by a method comprising the steps of:
I) applying to skin and hair affected by ectoparasites a water-soluble or water-dispersible, substantially air-impermeable, pharmacologically acceptable, liquid barrier composition containing one or more aralkyl alcohols in a quantity sufficient to prevent the ectoparasites from closing their respiratory systems;
II) leaving the composition in contact with the skin and hair until the ectoparasites have been killed by suffocation; and
III) removing the composition and the dead ectoparasites from the skin and hair.

The monohydric aralkyl alcohols used in the compositions and methods of the invention are those in which the hydroxyl group is attached to an alkyl group. The aryl moiety is preferably a phenyl or substituted phenyl group, although other aryl groups such as those with multiple rings are also within the scope of the invention provided the resulting aralkyl alcohol is pharmacologically compatible when applied as a component of compositions of the invention to animal skin and hair.

Preferred monohydric aralkyl alcohols of the invention are those having formula I below:

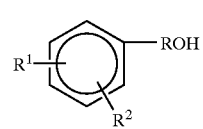

(I)

In which R is a $C_1$–$C_{12}$ straight or branched chain, saturated or olefinically unsaturated, alkylene group, and $R^1$ and $R^2$ are independently hydrogen, halogen (fluorine, chlorine, bromine, or iodine), $C_1$–$C_4$ alkyl, or $C_1$–$C_4$ alkoxy groups. Preferred compounds of formula I are those in which the R group is a $C_1$–$C_6$ saturated alkylene group, especially those wherein $R^1$ and $R^2$ are both hydrogen. The most preferred compound of formula I is benzyl alcohol. When the R group is an ethylenically unsaturated alkylene group, this group can also be referred to as an alkenylene group.

DETAILED DESCRIPTION OF THE INVENTION

It is to be understood that the compositions employed in the method of the invention described above kill the ectoparasites by suffocation as the only mechanism of action, and are accordingly free from pediculicides and other ingredients that would kill the parasites by mechanisms other than suffocation.

The ectoparasites treated by the methods and compositions of the invention include lice, especially head lice (*Pediculus humanus capitis*), as well as the crab (pubic) louse (*Phthirus pubis*) and the body or clothing louse (*Pediculus humanus humanus*); and mites (chiggers, scabies and the like).

The animal skin treated by the methods of the present invention include any skin area infected by an ectoparasite, especially those covered by hair, such as the human scalp and pubic area. Also, household pets and other animals infected with ectoparasites can also be treated by the methods of the invention.

It should be noted that other monohydric alcohols such as alkanols, e.g. ethanol and isopropyl alcohol, and polyhydric alcohols such glycols and polyalkylene glycols are not satisfactory for use in place of the monohydric aralkyl alcohols of the invention since they are not effective or are not completely effective in preventing the respiratory system of the ectoparasites from closing.

The water-soluble or water-dispersible, substantially air-impermeable, pharmacologically acceptable liquid barrier compositions containing one or more monohydric aralkyl alcohols used in the practice of the invention include any such compositions that are compatible with the skin, i.e. those that contain no components that are toxic or carcinogenic to the skin or any other parts of the animal if absorbed through the skin, including those that cause dermatitis, skin irritation, itching, or the like.

By substantially air-impermeable is meant that the composition does not contain sufficient air nor does it permit air to penetrate the composition in a quantity that would prevent the composition from suffocating the ectoparasites. It is of course the lack of oxygen over a period of time that results in the suffocation of the ectoparasites. Since the ectoparasites are killed by suffocation, they cannot become resistant to the compositions of the invention, unlike compositions containing insecticides.

The compositions must also be water-soluble or water dispersible so that they can be readily and rapidly removed by rinsing with water or other water-based liquid.

The compositions can be in the form of a free-flowing liquid to a viscous liquid or in the form of a gel.

The liquid barrier compositions of the invention preferably comprise the following components:
  A) at least one monohydric aralkyl alcohol;
  B) a film forming agent;
  C) a surface active agent;
  D) a thickening agent; and
  E) water Optional components can include (but are not limited to) the following:
  F) a neutralizing agent; and
  G) a preservative.

Component A) is present in a respiratory system closing prevention quantity. Such quantity usually ranges from 1 to 25% by weight, preferably from 2 to 10% by weight, more preferably from 3 to 7% by weight, and most preferably from 4 to 6% by weight, based on the weight of the liquid barrier composition. Quantities greater than 25% by weight are also effective, but are unnecessary. Quantities of less than 1% may be partially effective or may be effective over longer periods of time.

Component B) is present in from 1 to 25% by weight, preferably from 2 to 10% by weight, more preferably from 3 to 7% by weight, and most preferably from 4 to 6% by weight.

Component C) is present in from 0.1 to 10% by weight, preferably from 0.25 to 5% by weight, more preferably from 0.5 to 3% by weight, and most preferably from 0.8 to 1.2% by weight.

Component D) is present in from 0.05 to 5% by weight, preferably from 0.1 to 3% by weight, more preferably from 0.15 to 1% by weight, and most preferably from 0.2 to 0.35% by weight.

The remainder is component E), (water), optionally with small quantities of a neutralizing agent to adjust the pH to neutral or close to neutral, and/or other optional components such as small quantities (e.g. 0.01 to 1% by weight) of one or more preservatives.

The film forming agents of component B) include one or more of mineral oil (liquid petroleum) and other oils such as vegetable oils, e.g. cottonseed, coconut, palm, and the like, and other pharmacologically compatible oils such as other refined aliphatic petroleum oils, animal oils, e.g. fish oils, oleic acid, sperm oil, and oils derived from fruits and seeds such as corn, olive, soybean, cottonseed, safflower, and the like. Mineral oil is preferred.

The surface active agent of component C) is preferably one or more sugar-based surfactants, e.g. alkyl polyglycosides and glucosamides such as glucosamine and related compounds. The alkyl polyglycosides have the formula II below:

$$R_1O(R_2O)_b(Z)_a \qquad (II)$$

wherein $R_1$ is a monovalent organic radical having from about 6 to about 30 carbon atoms, preferably from 6 to 12 carbon atoms, and more preferably having an average of from 10 to 10.5 carbon atoms; $R_2$ is a divalent alkylene radical having from 2 to 4 carbon atoms; Z is saccharide residue having 5 or 6 carbon atoms; b is a number having a value from 0 to about 12; a is a number having a value from 1 to about 6, preferably from 1.2 to 2.2, and more preferably from 1.5 to 1.7. Preferred alkyl polyglycosides which can be used in the compositions according to the invention have the formula II wherein Z is or includes a glucose residue. Such alkyl polyglycosides are commercially available, for example; as TRITON® GC-110, an oligmeric D-glucopyranose decyl octyl glycoside from Union Carbide Corporation, and APG®, GLUCOPON®, or PLANTAREN® surfactants from Cognis Corporation, Ambler, Pa., 19002. Examples of the Cognis surfactants include but are not limited to:

1. GLUCOPON® 225DK Surfactant—an alkyl polyglycoside in which the alkyl group contains 8 to 10 carbon atoms and having an average degree of polymerization of 1.7.
2. GLUCOPON® 425N Surfactant—an alkyl polyglycoside in which the alkyl group contains 8 to 16 carbon atoms, having an average of 10.3 carbon atoms, and having an average degree of polymerization of 1.5.
3. GLUCOPON® 625UP Surfactant—an alkyl polyglycoside in which the alkyl group contains 12 to 16 carbon atoms and having an average degree of polymerization of 1.6.
4. APG® 325N Surfactant—an alkyl polyglycoside in which the alkyl group contains 9 to 11 carbon atoms and having an average degree of polymerization of 1.5.
5. GLUCOPON® 600UP Surfactant—an alkyl polyglycoside in which the alkyl group contains 12 to 16 carbon atoms and having an average degree of polymerization of 1.4.
6. PLANTAREN® 2000 Surfactant—a $C_8$–$C_{16}$ alkyl polyglycoside in which the alkyl group contains 8 to 16 carbon atoms and having an average degree of polymerization of 1.5.
7. PLANTAREN® 1300 Surfactant—a $C_{12}$–$C_{16}$ alkyl polyglycoside in which the alkyl group contains 12 to 16 carbon atoms and having an average degree of polymerization of 1.6.
8. GLUCOPON® 220N Surfactant—an alkyl polyglycoside in which the alkyl group contains 8 to 10 carbon atoms and having an average degree of polymerization of 1.5.

Other examples of alkyl polyglycosides that can be used herein include alkyl polyglycoside surfactants which are comprised of mixtures of compounds of formula II wherein Z represents a moiety derived from a reducing saccharide containing 5 or 6 carbon atoms; a is a number having a value from 1 to about 6; b is zero; and $R^1$ is an alkyl radical having from 8 to 20 carbon atoms. The compositions are characterized in that they have increased surfactant properties and an HLB in the range of about 10 to about 16 and a non-Flory distribution of glycosides, which is comprised of a mixture of an alkyl monoglycoside and a mixture of alkyl polyglycosides having varying degrees of polymerization of 2 and higher in progressively decreasing amounts, in which the amount by weight of polyglycoside having a degree of polymerization of 2 or mixtures thereof with the polyglycoside having a degree of polymerization of 3 predominate in relation to the amount of monoglycoside, said composition having an average degree of polymerization of about 1.8 to about 3. Such compositions, also known as peaked alkyl polyglycosides, can be prepared by separation of the monoglycoside from the original reaction mixture of alkyl monoglycoside and alkyl polyglycoside after removal of the alcohol. This separation may be carried out by molecular distillation and normally results in the removal of about 70–95% by weight of the alkyl monoglycosides. After removal of the alkyl monoglycosides, the relative distribution of the various components, mono- and poly-glycosides, in the resulting product changes and the concentration in the product of the polyglycosides relative to the monoglycoside increases as well as the concentration of individual polyglycosides to the total, i.e. DP2 and DP3 fractions in relation to the sum of all DP fractions. Such compositions are disclosed in U.S. Pat. No. 5,266,690, the entire contents of which are incorporated herein by reference.

The most preferred alkyl polyglycoside for use in the present invention is TRITON® GC-110.

While the sugar-based surfactants are preferred for use herein, other surface active agents can also be used, either in place of, or in addition to, the sugar-based surfactants. Examples of such other surfactants are disclosed in U.S. Pat. No. 6,139,859, which is expressly incorporated herein by reference.

The thickening agents of component D) include polyacrylic acid polymers, available from B. F. Goodrich Chemical Corporation as CARBOPOL® polymers. CARBOPOL® 940 is a water-soluble polyacrylic acid polymer which acts as a thickener and gel-former and is preferred for use herein.

Other thickening agents that can be used include, but are not limited to, sodium carboxymethyl-cellulose, ethoxylated cellulose, hydroxy-propylcellulose, hydroxyethyl cellulose, glyceryl monostearate, hydroxyethyl stearyl amide, ethylene glycol monostearate, stearic diethanolamide, coconut fatty acid diethanolamide, lauric diethanolamide, lauric/myristic diethanolamide, guar hydroxypropyl trimonium chloride, ethylene glycol distearate, n-octadecanol, lauric monoisopropanolamide, isostearamidopropyl betaine, PEG (400–1000) mono- or di- stearates, glycerol dioleate, alkali metal alginates, xanthan gum, and the like.

With respect to component F), when the composition has a pH of less than 7, triethanolamine or other pharmacologically compatible bases can be used as a neutralizing agent.

The component G) preservatives can be used if needed. For example, when component A) is benzyl alcohol, the benzyl alcohol also acts as a preservative. Other preservatives can be added if desired, such as parabens, imidurea, and the like.

With respect to component E) (water), preferred are compositions in which the quantity of water is in the range of from 80 to 90% by weight, more preferably from 85 to 89% by weight, and most preferably from 87 to 88.5% by weight.

The compositions of the invention can be prepared by adding components A), B) and C) to component E) at room temperature with mixing. Then component D) is added with mixing, followed by optional components F) and G) if needed or desired. The pH of the mixture is preferably 7±0.5.

With respect to the method of treatment described in the SUMMARY OF THE INVENTION, in step I) a coating of the composition is applied to the infected skin (and hair), either by hand or by a suitable applicator. In the case of head lice, the composition is massaged onto human dry hair and scalp.

In step II), the composition is allowed to remain in contact with the scalp or other skin area until the parasites are dead from suffocation, e.g. from 10 to 45 minutes, preferably from 10 to 15 minutes.

In step III), the composition is then readily and rapidly removed, e.g. by rinsing with water.

The above treatment will kill all motile stages of the lice and other ectoparasites, but the nits (eggs) are not easily destroyed, and hence a repeat treatment will probably be necessary, i.e. the above procedure is repeated once or twice after seven to ten day intervals, to kill any lice that may have hatched from adherent nits. Usually, the above procedure need only be repeated once.

However, a composition of the invention can be used in the above method which will also remove at least some of the nits as well as killing the ectoparasites. The basic composition is the same water-soluble or water-dispersible, substantially air-impermeable, pharmacologically acceptable, liquid barrier used in the above-described method of the invention. As an additional component or as a separate treatment, one or more substances that remove nits by loosening the adhesive bond that fastens the nits to the skin or hair is added or used in a separate treatment. Such substances include enzymes that loosen the nits by differential hydration. Such enzymes include one or more of oxidoreductase, transferase, lyase, hydrolase, isomerase, and ligase. Concentrations of such substances that are at least partially effective for removing nits depend on the particular substance chosen, but generally range from 0.0001 to 10% by weight of the composition.

The invention will be illustrated but not limited by the following examples.

EXAMPLES

Example 1

The following composition was prepared:

| Component | % by weight |
|---|---|
| Distilled water | 88.25 |
| Benzyl Alcohol, NF | 5.00 |
| Mineral Oil, NF | 5.00 |
| TRITON ® GC-110 | 1.00 |
| CARBOPOL ® 940, NF | 0.25 |
| Trolamine, NF * | 0.50 |
| | 100.00 |

* triethanolamine - added in the quantity shown or until a pH of 7 ± 0.5 is obtained.

The above composition was prepared by adding the benzyl alcohol, mineral oil and TRITON® GC-110 to the distilled water with mixing. Then the CARBOPOL® 940 was added with vigorous mixing for 30 minutes. Trolamine was added slowly with slow mixing until a pH of 7.0±0.5 was obtained. The mixture was in the form of a gel. Slow mixing was continued until the gel was uniform to minimize air entrapment.

Example 2

The following composition was prepared:

| Component | % by weight |
|---|---|
| Distilled water | 88.25 |
| Benzyl Alcohol, NF | 5.00 |
| Mineral Oil, NF | 5.00 |
| TRITON ® GC-110 | 1.00 |
| CARBOPOL ® 940, NF | 0.25 |
| Trolamine, NF* | 0.50 |
| Methylparaben, NF | 0.15 |
| Propylparaben, NF | 0.05 |
| Imidurea, NF | 0.20 |
| | 100.00 |

*triethanolamine - added in the quantity shown or until a pH of 7 ± 0.5 is obtained.

The above composition was prepared by heating the distilled water to 70° C. and adding the methylparaben, propylparaben and imidurea with mixing until the solids dissolved. The mixture was cooled to room temperature. Then the benzyl alcohol, mineral oil and TRITON® GC-110 were added with mixing. The CARBOPOL® 940 was added with vigorous mixing for 30 minutes. Trolamine was added slowly with slow mixing until a pH of 7.0±0.5 was obtained. The mixture was in the form of a gel. Slow mixing was continued until the gel was uniform to minimize air entrapment.

Example 3

The composition of Example 1 was prepared, to which is then added with mixing 10% by weight, based on the weight of the composition, of 1% by weight of a combination of oxidoreductase, transferase, lyase, hydrolase, isomerase, and ligase in 9% by weight of water.

Example 4

The composition of Example 1 was evaluated clinically, according to the following protocol:

After informed consent was obtained, twenty participants were enrolled in the study. Nineteen subjects completed all visits. One subject was dropped from the study after her mother shaved her head due to the "no nit policy" at the child's school.

Prior to treatment (Day 1), participants were visually evaluated for the number of viable lice and nits prior to treatment. A timed ten-minute application of the study product was then applied to thoroughly saturate the subject's hair (1–2 bottles depending on length). Immediately afterwards, the hair was rinsed with water, shampooed, rinsed and combed (with a wide-toothed comb). The rinse water was strained through a flour sack, cotton kitchen towel to collect and count the number of live or dead lice and nymphs present after the procedure.

One week later (Day 8), the above procedures were repeated for each subject. Therefore, each subject had two, ten-minute treatments one week apart in order to kill any nymphs that might have hatched after treatment.

A final evaluation was conducted on Day 15 through visual inspection. Nit removal was not conducted during the two-week study period. There were no adverse experiences (AE), and subject comments reflected satisfaction with regard to safety, efficacy and cosmetic acceptability.

There were a total of 20 females enrolled in the study. Most were heavily infested, some with hundreds of lice. Participants ranged from 5 to 35 years of age and had a mean age of 11.55 years (±8.19 years). The mean height for all participants was 128.93 cm (±20.97 cm). The mean weight from all participants was 88.61 lbs (±42.3 lbs). See Table 1 below.

TABLE 1

| Demographic Profile | | | | | | |
|---|---|---|---|---|---|---|
| Age Range (years) | Mean Age (years) | Std. Dev. Of Ages | Mean Height (cm) | Std. Dev. Of Heights | Mean Weight (lbs.) | Std. Dev. Of Weights |
| 5 to 35 | 11.55 | ±8.19 | 128.93 | ±20.97 | 88.61 | ±42.3 |

Methods

The protocol and informed consent was approved by the Southern IRB, Miami, Fla. The study was conducted at Lice Source Services from Oct. 4–25, 2001. Informed consent was obtained from subjects or their parents/guardians prior to enrollment. Participation was voluntary. Subject eligibility was determined by the presence of at least 5 live lice detected by visual inspection. Family members were included if they fit the eligibility criteria. This was an open-label pilot study, and all patients received the same treatment. See Tables 2 and 3 for baseline data.

The Lice Source Service investigation team administered all treatments. Safety was evaluated by a scalp examination conducted before initial treatment and immediately after each treatment.

Pediculicidal efficacy was determined by the absence of live lice on day 8 (±1 day) and day 15 (±2 days) after initial treatment. After the first and second treatments, the rinse water was collected and strained through a flour-sack kitchen towel. The towels were examined for any lice using a 6× lighted magnifier. If the subject had no live lice at the end of the study (day 15) they were scored as a TREATMENT SUCCESS.

The shampoo, comb, rinse, and straining method has been found, in our experience, to be more accurate in detecting lice than visual inspection. The number of lice and nymphs and their viability was recorded on the CRF.

TABLE 2

Severity of Infestations of Subjects at Baseline

| Severity | Lice* | Nits** |
|---|---|---|
| Mild | 5 | 0 |
| Moderate | 5 | 2 |
| Severe | 9 | 17 |
| Total | 19 | 19 |

*Lice: <10 = Mild; 10–15 = Moderate; >15 = Severe
**Nits: <10 = Mild; 11–19 = Moderate; 20–100's = Severe

TABLE 3

Stages of Lice in Subjects at Baseline

| | All |
|---|---|
| Adults Only | 1 |
| Nymphs Only | 0 |
| All Stages | 18 |
| Total | 19 |

Results

As per the study protocol, pediculicidal activity was assessed at Day 8. Eighteen subjects had no live lice at Day 8. The other remaining subject had one live nymph, indicating that the product appears to have excellent ovicidal activity. All study participants were evaluated at Day 8, and were given a second treatment regardless of whether or not they had live lice. At the final follow up (Day 15), each participant was determined to be a treatment success. See Table 4 below.

TABLE 4

Treatment Success Rates of the Composition of Example 1

| Total # of completed | Rx Success at Day 15 | % Rx Success at Day 15 |
|---|---|---|
| 19 | 19 | 100% |

Conclusions

This open label pilot study in a population heavily infested with *Pediculus capitis* demonstrates that two treatments of 10 minutes each of the composition of Example 1 was 100% effective. The product had excellent cosmetic acceptability by the LSS staff and the participants since it had no odor, was easy to use, and left the hair shiny and manageable.

What is claimed is:

1. In a water-soluble or water-dispersible, substantially air-impermeable, pharmacologically acceptable, liquid or gel form barrier composition containing a surfactant and a thickening agent, the improvement wherein the composition contains a quantity of at least one monohydric aralkyl alcohol of formula I below:

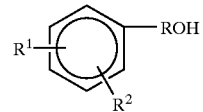

(I)

wherein R is a $C_1$–$C_{12}$ straight chain saturated alkylene group, and $R^1$ and $R^2$ are independently selected from the group consisting of hydrogen and $C_1$–$C_4$ alkyl groups sufficient to prevent lice from closing their respiratory systems when the composition is applied to an animal body infected with the lice; and wherein the composition is free from pediculicides.

2. The composition of claim 1 wherein the composition contains from about 1 to about 25% by weight of at least one monohydric aralkyl alcohol of formula I, based on the weight of the composition.

3. The composition of claim 1 wherein the composition contains an effective quantity of at least one enzyme that loosens nits.

4. The composition of claim 1 wherein the composition contains from about 2 to about 10% by weight of at least one monohydric aralkyl alcohol of Formula I.

5. The composition of claim 1 wherein the composition contains from about 3 to about 7% by weight of at least one monohydric aralkyl alcohol of Formula I.

6. The composition of claim 1 wherein the composition contains from about 4 to about 6% by weight of at least one monohydric aralkyl alcohol of Formula I.

7. The composition of claim 1 wherein the composition is a water-containing gel.

8. The composition of claim 1 wherein R in formula I is a $C_1$–$C_6$ saturated straight chain alkylene group.

9. The composition of claim 1 wherein the compound of formula I is benzyl alcohol.

10. The composition of claim 9 wherein the composition contains from about 1 to about 25% by weight of benzyl alcohol.

11. The composition of claim 9 wherein the composition contains from about 2 to about 10% by weight of benzyl alcohol.

12. A water-soluble or water-dispersible, substantially air-impermeable, pharmacologically acceptable, liquid barrier composition for killing lice infestations on the animal body comprising the following components:

A) at least one aralkyl alcohol in a quantity sufficient to prevent the lice from closing their respiratory system;
B) a film forming agent;
C) a surface active agent;
D) a thickening agent; and
E) water; and wherein the composition is free from pediculicides and wherein the at least one aralkyl alcohol has the formula I below

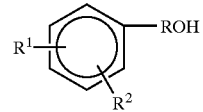

(I)

wherein R is a $C_1$–$C_{12}$ straight chain saturated alkylene group and $R^1$ and $R^2$ are independently selected from the group consisting of hydrogen and $C_1$–$C_4$ alkyl groups.

13. The composition of claim 12 in which component A) is present in a quantity sufficient to prevent a head louse from closing its spiracle.

14. The composition of claim 13 wherein the animal body is the body of a human being.

15. The composition of claim 12 wherein component A) is present in from about 1 to about 25% by weight of the composition.

16. The composition of claim 12 wherein component A) is present in from about 1 to about 25% by weight; component B) is present in from about 1 to about 25% by weight; component C) is present in from about 0.1 to about 10% by weight; and component D) is present in from about 0.05 to about 5% by weight, based on the weight of the composition.

17. The composition of claim 12 wherein component A) is present in from about 2 to about 10% by weight; component B) is present in from about 2 to about 10% by weight; component C) is present in from about 0.25 to about 5% by weight; and component D) is present in from about 0.1 to about 3% by weight; based on the weight of the composition.

18. The composition of claim 12 wherein component A) is present in from about 3 to about 7% by weight; component B) is present in from about 3 to about 7% by weight; component C) is present in from about 0.5 to about 3% by weight; and component D) is present in from about 0.15 to about 1% by weight; based on the weight of the composition.

19. The composition of claim 12 wherein component A) is present in from about 4 to about 6% by weight; component B) is present in from about 4 to about 6% by weight; component C) is present in from about 0.8 to about 1.2% by weight; and component D) is present in from about 0.2 to about 0.35% by weight; based on the weight of the composition.

20. The composition of claim 12 wherein R in Formula I is a $C_1$–$C_6$ saturated straight chain alkylene group.

21. The composition of claim 12 wherein the compound of formula I is benzyl alcohol.

22. The composition of claim 21 wherein the composition contains from about 1 to about 25% by weight of benzyl alcohol.

23. The composition of claim 21 wherein the composition contains from about 2 to about 10% by weight of benzyl alcohol.

24. The composition of claim 12 wherein component C) is a sugar-based surfactant.

25. The composition of claim 12 wherein component B) is an oil and component C) is an alkyl polyglycoside.

26. The composition of claim 13 wherein component E) is present in from about 80 to about 90% by weight, based on the weight of the composition.

27. The composition of claim 12 wherein the composition consists of the following components:

| Component | % by weight |
| --- | --- |
| Distilled water | about 88 |
| Benzyl alcohol | about 5 |
| Mineral oil | about 5 |
| Alkyl polyglycoside | about 1 |

-continued

| Component | % by weight |
| --- | --- |
| Thickening agent | about 0.25 |
| Triethanolamine | about 0.5. |

28. A method for the topical treatment of lice on animal skin comprising the steps of:
  A) applying to the skin and hair containing lice a water-soluble or water-dispersible, substantially air-impermeable, pharmacologically acceptable, liquid barrier composition containing a quantity of at least one monohydric aralkyl alcohol sufficient to prevent the lice from closing their breathing apparatus, wherein the liquid composition can range from free-flowing to gel form, and wherein the composition is free from pediculicides, and wherein the at least one monohydric aralkyl alcohol has the formula I below

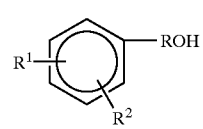

(I)

wherein R is a $C_1$–$C_{12}$ straight chain saturated alkylene group, and $R^1$ and $R^2$ are independently selected from the group consisting of hydrogen and $C_1$–$C_4$ alkyl groups;
  B) leaving the composition in contact with the skin and hair for at least 10 minutes until the lice have been killed by suffocation; and
  C) removing the composition and the dead lice from the skin and hair.

29. The method of claim 28 wherein the lice is the head louse.

30. The method of claim 28 wherein the composition also contains an effective quantity of at least one enzyme that loosens nits.

31. The method of claim 28 wherein the composition is in the form of a gel.

32. The method of claim 28 wherein the time period is from about 10 minutes to about 45 minutes.

33. The method of claim 28 wherein in step C) the composition is removed by rinsing with water.

34. The method of claim 28 wherein R in Formula I is a $C_1$–$C_6$ saturated sraight chain alkylene group.

35. The method of claim 28 wherein the compound of Formula I is benzyl alcohol.

36. The method of claim 28 wherein the composition contains from about 1 to about 25% by weight of benzyl alcohol.

37. The method of claim 28 wherein the composition contains from about 2 to about 10% by weight of benzyl alcohol.

38. The method of claim 28 wherein the composition is the composition of claim 12.

* * * * *